United States Patent
Marraccini et al.

[11] Patent Number: 4,962,282
[45] Date of Patent: Oct. 9, 1990

[54] DIRECT FLUORINATION OF FLUORO-BETA-SULTONES IN ORDER TO PRODUCE THE CORRESPONDING FLUOROOXY-FLUOROSULFONYL-FLUORO-COMPOUNDS

[75] Inventors: Antonio Marraccini, Novara; Gabriele Perego, Torino, both of Italy

[73] Assignee: Ausimont S.r.l., Milan, Italy

[21] Appl. No.: 479,518

[22] Filed: Feb. 13, 1990

[30] Foreign Application Priority Data

Feb. 13, 1989 [IT]  Italy ................................ 19425 A/89

[51] Int. Cl.$^5$ ........................................... C07C 303/02
[52] U.S. Cl. .................................................... 562/825
[58] Field of Search ......................................... 562/825

[56] References Cited

U.S. PATENT DOCUMENTS

| | | | |
|---|---|---|---|
| 3,041,317 | 6/1962 | Gibbs et al. | 562/825 |
| 3,714,245 | 1/1973 | Beckerbauer | 562/825 |
| 3,718,627 | 2/1973 | Grot | 562/825 |
| 4,476,058 | 10/1984 | Millauer et al. | 562/825 |
| 4,801,409 | 1/1989 | Marraccini et al. | 562/825 |

FOREIGN PATENT DOCUMENTS 52-10221  1/1977  Japan .................................... 562/825

*Primary Examiner*—James H. Reamer
*Attorney, Agent, or Firm*—Stevens, Davis, Miller & Mosher

[57] ABSTRACT

Preparation of fluorooxy-fluorosulfonyl-fluorocompounds by means of the direct fluorination with elemental fluorine of various $\beta$-sultones according to the following reaction scheme:

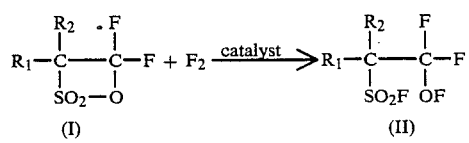

wherein $R_1$ and $R_2$, which can be either equal to, or different from, each other, represent a fluorine or chlorine atom, or an alkyl radical partially or totally halogenated with fluorine and/or chlorine.

The reaction takes place in continuous in the presence of a fluorination catalyst, preferably constituted by an alkali-metal fluoride preferably supported on a metal material, at temperatures comprised within the range of from $-30°$ C. to $+100°$ C., and under the pressure comprised within the range of from 50 to 800 kPa; said catalyst is a fixed-bed catalyst, or is suspended in a reaction medium inert under the operating conditions.

14 Claims, No Drawings

DIRECT FLUORINATION OF FLUORO-BETA-SULTONES IN ORDER TO PRODUCE THE CORRESPONDING FLUOROOXY-FLUOROSULFONYL-FLUORO-COMPOUNDS

DESCRIPTION OF THE INVENTION

The present invention relates to a process for preparing fluorooxy-fluorosulfonyl-fluorocompounds according to the following reaction scheme:

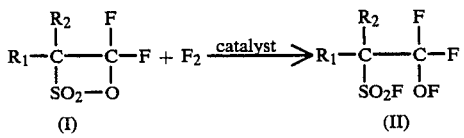

wherein $R_1$ and $R_2$, which can be either equal to, or different from, each other, represent a fluorine or chlorine atom, or an alkyl radical partially or totally halogenated with fluorine and/or chlorine.

The fluorooxy-fluorosulfonyl-fluorocompounds can find several uses. For example, they are used as fluorinating agents. In particular, they can be furthermore reacted with chlorofluorinated olefins, such as, e.g., 1,2-dichlorodifluoro-ethylene, in order to obtain an ether adduct from which, by means of a dechlorination, a fluorosulfonylperhaloalkyl-vinyl-ether can be prepared, which is a monomer for ion-exchange copolymers used as membranes, e.g., for diaphragms for electrolytic cells for sodium hydroxide and chlorine production.

No processes are known from the prior art, which make it possible fluoro-β-sultones to be converted into the corresponding fluorooxy-fluorosulfonyl-fluorocoumpounds by means of one single reaction step.

It is known that fluoro-β-sultones can be isomerized into the corresponding fluorosulfonylfluoroacyl fluorides by means of the use of catalysts, in general of nucleophilic character, such as triethylamine, dibutylether, alkali-metal fluorides, and so forth, or by heating at 80° C. for one hour in an autoclave [Angew. Chemie Int. Ed., 11 (1972) No. 7, 583; U.S. Pat. No. 4,466,881].

According to the prior art, when one starts from tetrafluoroethane-β-sultone, the reaction of isomerization proceeds as follows:

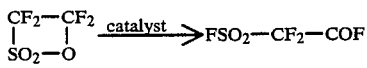

The so obtained fluorosulfonyldifluoroacetyl fluoride can be subsequently converted into the corresponding fluorooxy compound according to as disclosed in U.S. Pat. No. 4,801,409 to the same Applicant.

An object of the instant invention is therefore of providing a process which makes it possible the above said fluorooxy-fluorosulfonyl-fluorocompounds of formula (II) to be obtained by means of one single reaction step by starting from the corresponding fluoro-β-sultones, with the step of isomerization into acyl fluorides—i.e., products per se sensitive to hydrolysis, and which therefore require the adoption of particular handling measures—being avoided.

Another object is of obtaining the above said fluorooxy-fluorosulfonyl-fluorocompounds with very high yields, and with a high purity.

These objects are achieved by means of the process, according to the present invention, for preparing fluorooxy-fluorosulfonyl-fluorocompounds of formula:

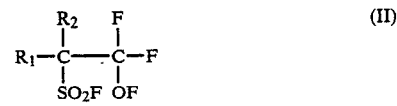

wherein $R_1$ and $R_2$, which can be either equal to, or different from, each other, represent a fluorine or chlorine atom, or an alkyl radical partially or totally halogenated with fluorine and/or chlorine, by causing a gaseous stream of fluorine and of a fluoro-β-sulfone of formula:

wherein $R_1$ and $R_2$ have the above stated meaning, to continuously flow, preferably together with an inert gas, on a fluorination catalyst, which catalyst is a fixed-bed catalyst, or is suspended in a liquid reaction medium or vehicle inert under the operating conditions, with the reaction product being continuously removed in the gas state from the same fluorination catalyst.

The average time of contact of the reactants with the catalyst is comprised within the range of from 1 second to 10 minutes, and the temperature is comprised within the range of from −40° C. to +100° C., and the pressure is comprised within the range of from 50 to 800 kPa.

By operating under the reaction conditions according to the present invention, the fluoro-β-sultones of formula (I) are directly converted, with very good yields, into the fluorooxy-fluorosulfonyl-fluorocompounds.

The process can be practically carried out with all of the known types of fluorination catalysts. Preferably, an alkali-metal fluoride, and, in particular, cesium fluoride or potassium fluoride, is used.

When a fixed-bed catalyst is used, said catalyst is preferably supported on a material capable of securing a good heat exchange, or it is mixed with such a material. Among the materials suitable for the intended purpose, e.g. copper and copper alloys, such as brass and Monel, can be mentioned.

When the catalyst is suspended in an inert, liquid reaction vehicle, or medium the reactants, mixed with an inert diluting gas, are bubbled through the liquid medium with this latter being simultaneously kept stirred in order to keep the catalyst homogeneously suspended.

The liquid medium is preferably a perfluoropolyether. Perfluoropolyethers are well-known compounds disclosed, e.g., in U.K. Pat. No. 1,104,482, and in U.S. Pat. Nos. 3,242,218; 3,665,041; and 3,715,378. The use of a catalyst suspended in a liquid medium is sometimes preferred, when a particularly unstable fluorooxy-fluorosulfonyl-perhaloalkane is prepared, because the liquid medium secures a better homogeneity of heat exchange, with overheatings of local character being thus prevented.

The reaction is carried out at a temperature comprised within the range of from −30° C. to +100° C. The operating reaction pressure is comprised within the range of from 50 to 800 kPa, with a pressure slightly higher than the atmospheric pressure being preferably used, with, i.e., a slight overpressure being maintained, which is suitable for causing the gas to flow through the fluorination reactor.

The reactants are preferably diluted with a transport gas inert under the reaction conditions. Commonly, the amount of this gas is such that the concentration of the reactants in the gas mixture is comprised within the range of from 5 to 70% by volume.

As the transport gas, nitrogen, helium, argon, or chlorofluorocarbons, such as tetrafluoromethane, dichlorotetrafluoroethanes and pentafluorochloroethane, can be used.

The molar ratio of fluorine to fluoro-β-sultone is comprised within the range of from 1.0 to 1.5.

The flow rate of each reactant is comprised within the range of from $5.10^{-6}$ up to 1 mol/hour per each catalyst gram, and is preferably comprised within the range of from $10^{-4}$ up to $10^{-1}$ mol/hour per each catalyst gram.

In the fluoro-β-sultone used as the starting material, the $R_1$ and $R_2$ radicals, which can be either equal to, or different from, each other, preferably represent a fluorine atom, or a perhaloalkyl radical containing from 1 to 10 carbon atoms; more preferably, the perhaloalkyl radical contains from 1 to 3 carbon atoms.

The fluoro-β-sultones in which either, or both, of $R_1$ and $R_2$ radicals represent a perfluoroalkyl radical of from 1 to 3 carbon atoms, are particularly preferred; when only one of said $R_1$ and $R_2$ radicals has this latter meaning, the other one is a fluorine atom.

In the case of tetrafluoroethane-β-sultone ($R_1=R_2=F$), the reaction proceeds according to the following reaction scheme:

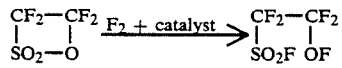

Examples of fluoro-β-sultones suitable for being used in the process according to the present invention are the following:
(1) 3,3,4,4-tetrafluoro-2,2-dioxido-1,2-oxathioethane;
(2) 3,4,4,-trifluoro-3-chloro-2,2-dioxido-1,2-oxathioethane;
(3) 3,4,4,-trifluoro-3-trifluoromethyl-2,2-dioxido-1,2-oxathioethane;
(4) 3,4,4,-trifluoro-3-(1,1,2,2,3,3,4,4,5,5,6,6-dodecafluorohexyl)-2,2-dioxido-1,2-oxathioethane.

The following non-limitative examples are supplied for the purpose of illustrating the invention.

EXAMPLE 1

250 ml of tetrafluoroethane-β-sultone was charged to a bubbler of 500 ml of capacity, and the whole was cooled down to 0° C. By means of a candle of sintered glass a stream of 1.0 l/hour of $N_2$ was flown through said bubbler. The nitrogen stream left the bubbler enriched with vapours of β-sultone. After a further dilution with 10.0 l/hour of $N_2$, the β-sultone-containing gas stream was mixed with a stream of 1.5 l/hour of $F_2$, and the mixture was continuously fed to a cylindrical reactor of AISI 316 steel, of 130 cm³ of capacity, completely filled with small copper needles, mixed with 50 g of CsF, previously ground and thoroughly dried. The temperature of such a reactor was adjusted and controlled at the constant temperature of +25° C. by circulating a liquid inside the outer jacket the same reactor was provided with.

The time of contact of the gases with the catalyst was of about 70 seconds.

Within a run time of 70 hours, 44 g of tetrafluoroethane-β-sultone resulted to have been eliminated, as determined by weighing the bubbler before beginning, and after ending, the test run.

The mixture leaving the reactor, analysed by means of an in-line I.R. spectrophotomer, showed the nearly total disappearance of the typical absorption bands of tetrafluoroethane-β-sultone within the range of from 1900 to 1980 cm$^{-1}$ and the appearing of the typical absorption bands of fluorooxy-fluorosulfonyl-tetrafluoroethane at 1460 cm$^{-1}$ ($FSO_2$—), between 1100 and 1340 cm$^{-1}$ and 896 cm$^{-1}$ (—OF).

The conversion of tetrafluoroethane-β-sultone results to be higher than 98%.

Also the check by $^{19}F$-N.M.R. is in accordance with the hypothesized structure: δOF = +152.4 ppm.

From the gas-mass analysis and the $^{19}F$-N.M.R. analysis of the products of addition of fluorooxy-fluorosulfonyl-tetrafluoroethane to 1,2-dichlorodifluoroethylene, it was possible to identify and isolate the addition product $$FSO_2CF_2CF_2OCFClCF_2Cl,$$

thus giving a further confirmation of the chemical nature of the above intermediate fluorooxy compound.

EXAMPLE 2

To the same reactor as of Example 1, the same mixture of reactant gases was fed under the same experimental conditions, but with a temperature of +80° C. being maintained inside the fluorination reactor.

The analytical check of the reaction products made it possible the conversion of tetrafluoroethane-β-sultone into fluorooxy fluorosulfonyltetrafluoroethane to be verified. Once again, values higher than 98% were obtained.

We claim:
1. Process for preparing, in one single reaction step, fluorooxy-fluorosulfonyl-fluorocompounds of formula:

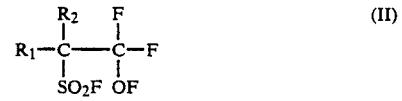
(II)

$R_1$ and $R_2$, which can be either equal to, or different from, each other, represent a fluorine or chlorine atom, or an alkyl radical partially or totally halogenated with fluorine and/or chlorine, characterized in that a gaseous stream constituted by a mixture of fluorine and of a fluoro-β-sultone of formula:

(I)

wherein $R_1$ and $R_2$ have the above stated meaning, is caused to continuously flow on a fluorination catalyst at temperatures comprised within the range of from $-30°$ C. up to $+100°$ C., and under pressures comprised within the range of from 50 to 800 kPa, with the reaction product being continuously removed from the same fluorination catalyst.

2. Process according to claim 1, wherein the fluorination catalyst is an alkali-metal fluoride.

3. Process according to claim 2, wherein the fluorination catalyst is selected from among potassium fluoride and cesium fluoride.

4. Process according to claim 1 wherein the fluorination catalyst is a fixed-bed catalyst.

5. Process according to claim 4, wherein the fixed-bed catalyst is supported on a material capable of supplying a good heat exchange.

6. Process according to claim 4, wherein the fixed-bed catalyst is mixed with a material capable of supplying a good heat exchange.

7. Process according to claim 5, wherein the material capable of supplying a good heat exchange is copper or copper alloys.

8. Process according to claim 1 wherein the fluorination catalyst is suspended in a liquid reaction medium inert under the reaction conditions.

9. Process according to claim 8, wherein the inert, liquid reaction medium is a perfluoropolyether.

10. Process according to claim 1 wherein the gaseous stream of the reactants is diluted with a transport gas inert under the reaction conditions.

11. Process according to claim 10, wherein the inert transport gas is selected from among nitrogen, helium, argon, fluorocarbons and fluorochlorocarbons.

12. Process according to claim 10, wherein the inert transport gas is used in an amount of from 30 to 95% by volume, as referred to the volume of the gas mixture.

13. Process according to claim 1 wherein the molar ratio of fluorine to fluoro-$\beta$-sultone is comprised within the range of from 1 to 1.5.

14. Process according to claim 6, wherein the material capable of supplying a good heat exchange is copper or copper alloys.

* * * * *